United States Patent [19]

Hanka et al.

[11] 4,282,327

[45] Aug. 4, 1981

[54] BIOLOGICALLY PURE CULTURE OF PAECILOMYCES ABRUPTUS

[75] Inventors: Ladislav J. Hanka; Paul F. Wiley, both of Kalamazoo, Mich.

[73] Assignee: The Upjohn Company, Kalamazoo, Mich.

[21] Appl. No.: 917,599

[22] Filed: Jun. 21, 1978

Related U.S. Application Data

[62] Division of Ser. No. 789,644, Apr. 22, 1977, Pat. No. 4,123,521.

[51] Int. Cl.³ .............................................. C12N 1/14
[52] U.S. Cl. ................................... 435/254; 435/171; 435/932
[58] Field of Search ................................ 435/254, 171

[56] References Cited

U.S. PATENT DOCUMENTS

| 3,303,094 | 2/1967 | Sokoloff et al. | 435/171 |
| 3,979,260 | 9/1976 | Nakao et al. | 435/47 |

*Primary Examiner*—Alvin E. Tanenholtz
*Attorney, Agent, or Firm*—Roman Saliwanchik

[57] ABSTRACT

New antibiotic U-53,946 produced by the controlled fermentation of the new microorganism *Paecilomyces abruptus* sp. nov., NRRL 11110. This antibiotic is active against Gram-positive bacteria, for example, *Sarcina lutea, Staphylococcus aureus, Bacillus subtilis, Mycobacterium avium,* and *Streptococcus pyogenes,* and the yeast *Saccharomyces pastorianus.* Accordingly, they can be used in various environments to eradicate or control these microorganisms.

1 Claim, 2 Drawing Figures

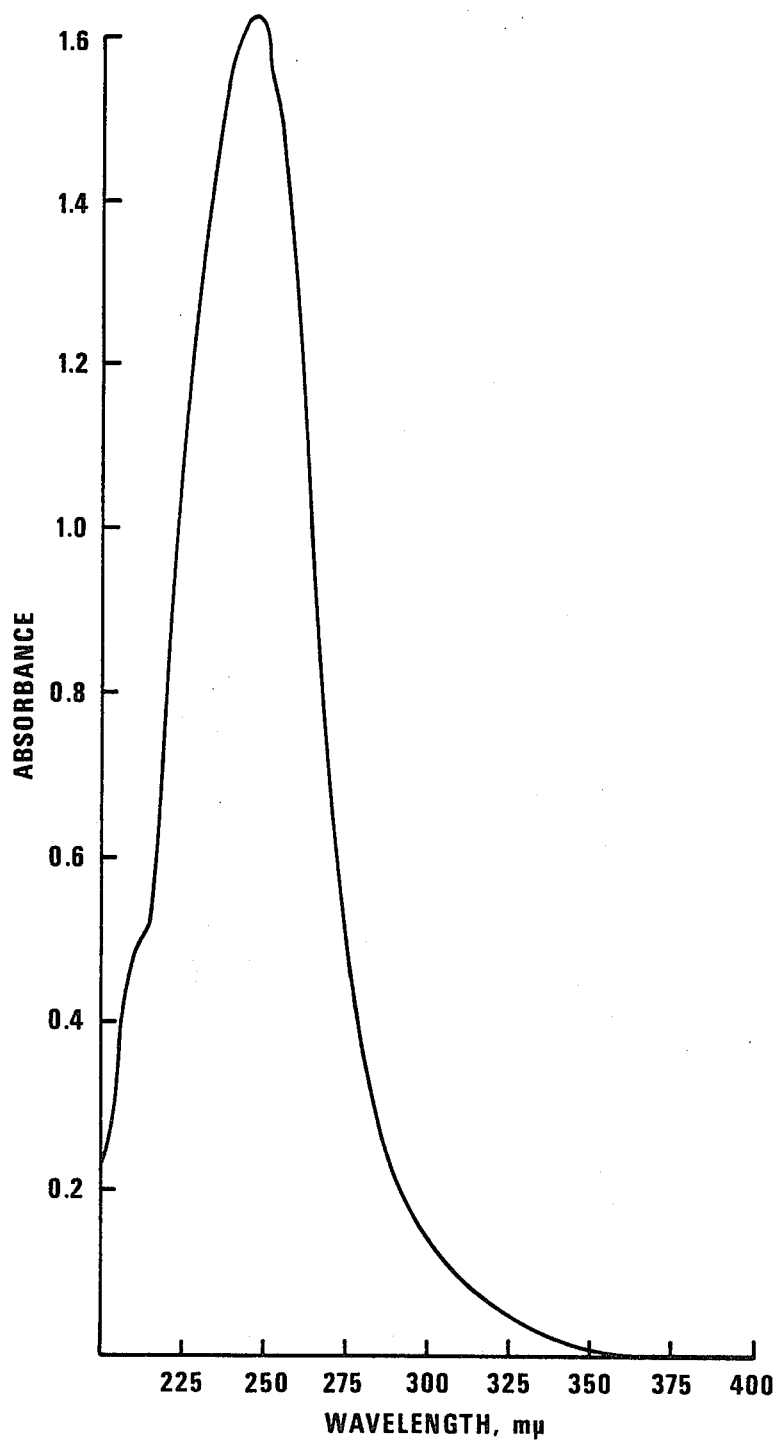

BIOLOGICALLY PURE CULTURE OF PAECILOMYCES ABRUPTUS

The invention described herein was made in the course of, or under Contract NO1-CM-43753 with the National Cancer Institute, National Institutes of Health, Bethesda, Maryland 20014.

This is a division of application Ser. No. 789,644, filed Apr. 22, 1977, now U.S. Pat. No. 4,123,521.

BRIEF SUMMARY OF THE INVENTION

The novel antibiotic of the invention, U-53,946 is obtained by culturing Paecilomyces abruptus sp. nov. NRRL 11,110, in an aqueous nutrient medium under aerobic conditions. Antibiotic U-53,946 has the property of adversely affecting the growth of Gram-positive bacteria, for example, S. aureus, S. lutea, B. subtilis, M. avium, and S. pyogenes. Accordingly, U-53,946 can be used alone or in combination with other antibiotic agents to prevent the growth of or reduce the number of bacteria, as disclosed above, in various environments.

DETAILED DESCRIPTION OF THE INVENTION

Chemical and Physical Properties of U-53,946

Molecular Formula: $C_{61}H_{107}N_{11}O_{14}$

Figure 1:
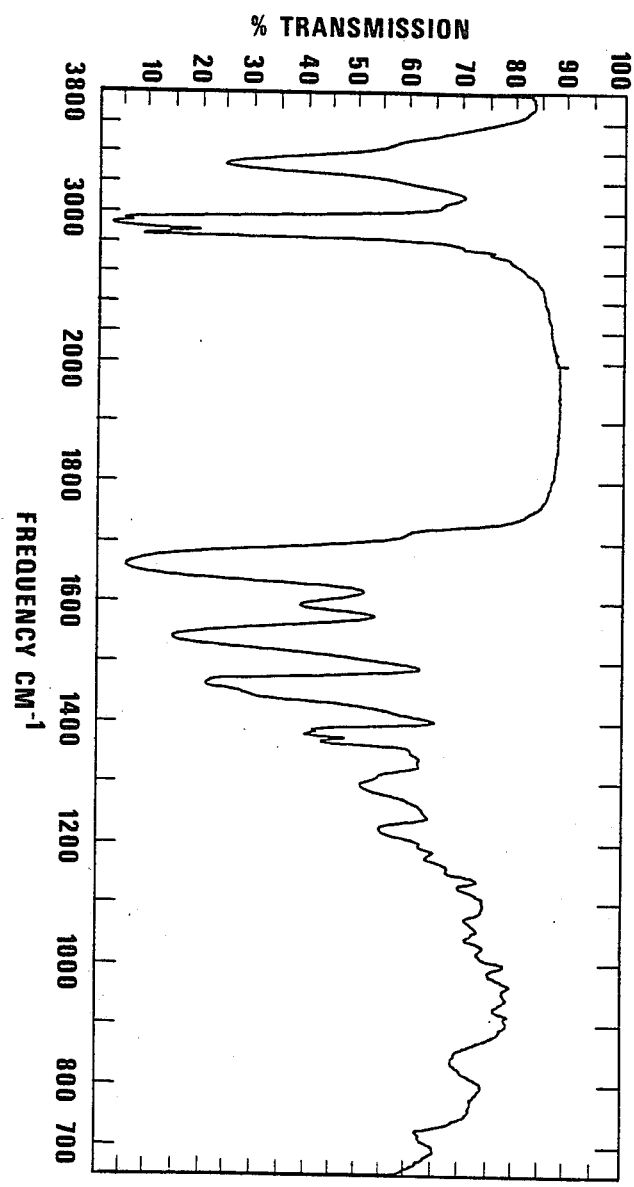

Elemental Analysis: Calcd.: C, 60.12; H, 8.85; N, 12.65; O, 18.38. Found: C, 60.13, 59.73; H, 9.21, 8.92; N, 12.16, 11.97; O, 18.44.

Molecular Weight: 1218±1 (Determined by mass spectrometry)

Melting Point: 200°–205° C.

Specific Rotation: $[\alpha]_D^{25} = -26°$ (c, 0.9175 EtOH)

Solubilities: Antibiotic U-53,946 is soluble in water and lower alcohols, for example, methanol and butanol; ketones, for example, methyl ethyl ketone, halogenated solvents, ethyl acetate, or other ester-type solvents; it is relatively insoluble in aliphatic hydrocarbons.

Antibiotic U-53,946 is a neutral compound.

Ultraviolet Absorption Spectra: In ethanol-max 245 nm $\epsilon$1510 (see FIG. 2 of the drawings). $R_f$: Antibiotic U-53,946 has an $R_f$ of 0.34 ($CHCl_3$—$CH_3OH$—$NH_4OH$; 85:14:1 v/v).

Infrared Absorption Spectrum: U-53,946 has a characteristic infrared absorption spectrum in a mineral oil mull as shown in FIG. 1 of the drawings. Peaks are observed at the following wave lengths expressed in reciprocal centimeters:

| Band Frequency (Wave Numbers) | Intensity | |
|---|---|---|
| 3450 | M, sh | (sh = shoulder) |
| 3320 | S | (S = strong) |
| 3040 | W | (M = medium) |
| 2950 | S | (W = weak) |
| 2920 | S | |
| 2850 | S | |
| 2730 | W | |
| 1710 | M, sh | |
| 1592 | M | |
| 1537 | S | |
| 1460 | S | |
| 1445 | M, sh | |
| 1385 | M | |
| 1377 | M | |
| 1365 | M | |
| 1307 | M | |
| 1292 | M | |
| 1223 | M | |
| 1190 | W | |
| 1173 | W | |
| 1150 | W | |
| 1125 | W | |
| 1070 | W | |
| 1037 | W | |
| 1015 | W | |
| 982 | W | |
| 952 | W | |
| 923 | W | |
| 908 | W | |
| 837 | W | |
| 720 | W | |
| 708 | W | |

Antimicrobial Activity of U-53,946

| Microorganism | Medium* | Zone of inhibition (mm) |
|---|---|---|
| Proteus vulgaris | 1 | 0 |
| Salmonella gallinarum | 1 | 0 |
| Pseudomonas aeruginosa | 1 | 0 |
| Salmonella schottmuelleri | 1 | 0 |
| Klebsiella pneumoniae | 2 | 0 |
| Sarcina lutea | 3 | 31 |
| Staphylococcus aureus | 1 | 25 |
| Bacillus subtilis | 2 | 25 |
| Mycobacterium avium | 4 | 30 |
| Streptococcus pyogenes | 4 | 33 |
| Saccharomyces pastorianus | 5 | 17 |
| Penicillium oxalicum | 6 | 0 |

*Medium 1(Nutrient Agar), 2(Streptomycin Assay Agar), 3(Seed Agar), 4(Brain Heart Infusion Agar), and 6(Malt Extract Agar) can be obtained from Difco Company, Detroit, Michigan. Medium 5(Gray's Agar) has the following ingredients:

| | Gm/liter $H_2O$ |
|---|---|
| Glucose | 30 |
| Yeast Extract | 7 |
| $KH_2PO_4$ | 5 |
| Agar | 15 |

The above antimicrobial spectrum was obtained by a standard disc plate method using 13 mm paper discs. The microorganisms were cultivated in media as shown beneath the results, supra. The preparation of U-53,946 was tested at a concentration of 1 mg/ml.

A solution of this preparation in water (0.08 mcg/ml) inhibited L 1210 cell growth in vitro by 90%.

THE MICROORGANISM

The microorganism used for the production of U-53,946 is Paecilomyces abruptus sp. nov., NRRL 11,110. A subculture of this microorganism can be obtained from the permanent collection of the Northern Regional Research Laboratory, U.S. Department of Agriculture, Peoria, Ill., U.S.A. It should be understood that the availability of the culture does not constitute a license to practice the subject invention in derogation of patent rights granted with the subject instrument by governmental action.

The microorganism of this invention was studied and characterized by Alma Dietz and Grace P. Li of The Upjohn Research Laboratories.

A soil isolate (designated CC-1014) was considered to belong to the Penicillium lilacinum Series of Raper and Thom's [Raper, K. B. and C. Thom. 1949. A Manual of the Penicillia. 875 pp. The Williams and Wilkins Co., Baltimore] section Assymmetrica, sub-section Divaricata or to the genus Paecilomyces. P. lilacinum and Paecilomyces both lack the green color associated with most penicillia but produce branched conidial structures like those found in Penicillium species. Therefore, the new isolate was compared with the P. lilacinum strain in our collection. The cultures showed aerial growth color similarities on most media but differed in reverse color and microscopic properties as may be noted in the tables that follow. Significant microscopic characteristics of the new culture are the appearance of a typical penicillus, a short (abrupt) conidiophore from which arise a cluster of 3-5 sterigmata of equal length. The sterigmata appear as tapered tubes which give rise to long chains of smooth surfaced elliptical spores. Another characteristic of the new isolate is the production of antibiotic U-53,946 (a cytotoxic agent, CC-1014).

DESCRIPTION

*Paecilomyces abruptus* Dietz and Li, sp. nov.

Color Characteristics. The appearance of the cultures on Ektachrome is given in Table 1. Reference Color Characteristics of the cultures on agar are given in Table 2.

Temperature Studies. Both cultures grew well at 18°-32° C. *Paecilomyces abruptus* grew well at 37° C. The properties cited for the new species are confirmatory for the *Penicillium lilacinum* series or the *Paecilomyces* group of Raper and Thom, supra. The *P. lilacinum* series is now assigned to the genus *Paecilomyces* [Index of Fungi. 1975. A List of Names of New Genera, Species and Varieties of Fungi and Lichens. New Combinations and New Names, Compiled from World Literature. 4: 283. Commonwealth Mycological Institute. Kew. Surrey.]. Macroscopic and microscopic properties noted for the new soil isolate enable it to be distinguished from the species assigned to this genus for which descriptions are available. Therefore, we propose that the new strain be designated *Paecilomyces abruptus* Dietz and Li, sp. nov. The species designation is based on the distinctive short (abrupt) conidiophores of this isolate.

*Paecilomyces lilacinus* grew poorly at 37° C. Good growth occurred when the plates were reincubated at 24° C. The cultures did not grow at 45° or 55° C. These temperatures were fungicidal.

Microscopic Characteristics. The cultures are compared in Table III.

METHODS

Macroscopic and microscopic growth characteristics were determined on media cited in Cooke [Cooke, W. B. 1963. A Laboratory Guide to Fungi in Polluted Waters, Sewage, and Sewage Treatment Systems. Their Identification and Culture. Public Health Service Publication No. 999-WP-1. U.S. Dept. of Health, Education, and Welfare. Public Health Service. Division of Water Supply and Pollution Control. Cincinnati 26, Ohio], Raper and Thom [Raper, K. B. and C. Thom. 1949. A Manual of the Penicillia. 875 pp. The Williams and Wilkins Co., Baltimore], and Smith [Smith, G. 1946. 3rd ed. An Introduction to Industrial Mycology. Edward Arnold and Co., Ltd., London. (Reprinted 1947. Jarrold and Sons, Ltd., Norwich)].

The soil isolate and *Paecilomyces lilacinus* (formerly *Penicillium lilacinum*) BB-156 (UC 4371), the culture in our collection to which the new isolate appeared most similar, were seeded from soil stocks to Gray's broth in shake flasks. The seeded flasks were incubated for 48 hours on a reciprocal shaker at 28° C. Growth in the shake flasks was blended for one minute at low speed in a Waring Blender. The blended inoculum was seeded on slants and plates. Agar slant media used were Neopeptone-Dextrose, Czapek's Sucrose, Leonian's, Water, Potato-Dextrose and Gray's. Agar plate media were: Czapek's Sucrose, Potato-Dextrose, Malt Extract for single plates and the same media plus Wort Agar for four-sector plates. Slants and single plates were incubated at 28° C. Four-sector plates were incubated at 18°, 24°, 28°, 32°, 37°, 45°, and 55° C.

The color pattern of the growth on the slant media was photographed on Ektachrome after seven days incubation at 28° C. Color determination of agar plate growth was made using the ISCC-NBS Centroid Color Charts (Supplement to NBS Circular 553 [Kelley, K. L. and D. B. Judd. 1955. The ISCC-NBS Method of Designating Colors and a Dictionary of Color Names. National Bureau of Standards Circular 553. Superintendant of Documents, U.S. Government Printing Office, Washington, D.C.]).

Microscopic characteristics were determined by dissecting microscope examination and by scanning electron microscope examination using the methods of Dietz and Mathews [Dietz, A. and J. Mathews. 1969. Scanning electron microscopy of selected members of the *Streptomyces hygroscopicus* group. Appl. Microbial. 18: 694-696].

NOTE: The designation "UC", which appears in this specification, prior to a number refers to The Upjohn Company Culture Collection and is a registered trademark.

TABLE I

| | | Appearance of Cultures on Ektachrome | |
|---|---|---|---|
| Agar Medium | Determination | Paecilomyces abruptus NRRL 11110 | Paecilomyces lilacinus BB-156, UC 4371 |
| Neopeptone-Dextrose | S | Lavender-gray | Lavender-gray |
| | R | Cream | Yellow-tan |
| Czapek's Sucrose | S | Lavender-gray-pink | Lavender-gray-pink |
| | R | Cream | Red-tan |
| Leonian's | S | Pink | Pink |
| | R | Pale pink | Pink-tan |
| Water | S | Trace lavender-pink | Trace lavender-pink |
| | R | Gray-pink | Gray-pink |
| Potato-Dextrose | S | Pink | Lavender-pink |
| | R | Cream-tan | Red-tan |
| Gray's | S | Lavender-pink | Lavender-pink |
| | R | Yellow-tan | Red-tan |

S = Surface color
R = Reverse color

TABLE II

| | | Reference Color Characteristics* | | | |
|---|---|---|---|---|---|
| | | Paecilomyces abruptus NRRL 11110 | | Paecilomyces lilacinus BB-156, UC 4371 | |
| Agar Medium | Determination | Chip No. | Color Description | Chip No. | Color Description |
| Czapek's Sucrose | S | 32 | Grayish yellowish pink | 9 | Pinkish white |
| | R | 9 | Pinkish white | 31 | Pale yellowish |

TABLE II-continued

| | | Reference Color Characteristics* | | | |
|---|---|---|---|---|---|
| | | Paecilomyces abruptus NRRL 11110 | | Paecilomyces lilacinus BB-156, UC 4371 | |
| Agar Medium | Determination | Chip No. | Color Description | Chip No. | Color Description |
| Gray's | S | 32 | Grayish yellowish pink | 9 | pink Pinkish white |
| | R | 89 | Pale yellow | 79 | Light grayish yellowish brown to |
| | | | | 46 | Grayish reddish brown |
| Malt Extract | S | 32 | Grayish yellowish pink | 9 | Pinkish white |
| | R | 33 | Brownish pink (center) | 73 | Pale orange yellow |
| | | 92 | Yellowish white (edge) | | |
| Potato-Dextrose | S | 32 | Grayish yellowish pink | 9 | Pinkish white |
| | R | 79 | Light grayish yellowish brown | 46 | Grayish reddish brown (trace) with |
| | | | | 33 | Brownish pink to |
| | | | | 20 | Dark grayish red to |
| | | | | 31 | Pale yellowish pink |
| Wort | S | 32 | Grayish yellowish pink | 9 | Pinkish white |
| | R | 58 | Moderate brown to | 70 | Light orange yellow |
| | | 76 | Light yellowish brown | | |

*Kelley, K.L. and D.B. Judd., supra.
S = Surface color
R = Reverse color

TABLE III

| | Microscopic Characteristics | |
|---|---|---|
| | Paecilomyces abruptus NRRL 11110 | Paecilomyces lilacinus BB-156, UC 4371 |
| Dissecting Microscope | | |
| Colony type | Velvety to lanose. | Velvety. |
| Colony growth | Rapid-difficult to determine edge. Central area raised and radically furrowed. | Rapid-difficult to determine edge. |
| Zonation | — | — |
| Exudate | Good to heavy on Czapek's sucrose and malt-extract agars. Poor on potato-dextrose agar. | Poor on Czapek's sucrose and malt-extract agars. Good on potato-dextrose agar. |
| Scanning Electron Microscope | | |
| Conidiophores | 7.5 × 2.5 μm. Smooth. Arise from substrate and aerial hyphae. May be terminal. | 7.5 × 2 μm. Smooth. Arise from substrate and aerial hyphae. May be terminal. |
| Metulae | Uncommon. | Uncommon. |
| Sterigmata | 3-5 Tapered. 7.0 × 2.5 μm to 7.0 × 1.0 μm. | Usually 2. Tapered. 7.0 × 2.0 μm to 7.0 × 0.7 μm. |
| Conidial chains | Parallel. | Not usually parallel. |
| Conidia | Smooth. 3.0 × 1.75 μm. Ridged appearance from 2-sided dimpling. | Smooth. 2 × 1.25 μm. Ridged appearance from 2-sided dimpling. |
| Sclerotia | Not detected. | Not detected. |
| Perithecia | Not detected. | Not detected. |
| Ascospores | Not detected. | Not detected. |

The new compound of the invention is produced when the elaborating organism is grown in an aqueous nutrient medium under submerged aerobic conditions. It is to be understood, also, that for the preparation of limited amounts surface cultures and bottles can be employed. The organism is grown in a nutrient medium containing a carbon source, for example, an assimilable carbohydrate, and a nitrogen source, for example, an assimilable nitrogen compound or proteinaceous material. Preferred carbon sources include glucose, brown sugar, sucrose, glycerol, starch, cornstarch, lactose, dextrin, molasses, and the like. Preferred nitrogen sources include cornsteep liquor, yeast, autolyzed brewer's yeast with milk solids, soybean meal, cottonseed meal, cornmeal, milk solids, pancreatic digest of casein, fish meal, distillers' solids, animal peptone liquors, meat and bone scraps, and the like. Combinations of these carbon and nitrogen sources can be used advantageously. Trace metals, for example, zinc, magnesium, manganese, cobalt, iron, and the like, need not be added to the fermentation media since tap water and unpurified ingredients are used as components of the medium prior to sterilization of the medium.

Production of the compound of the invention can be effected at any temperature conducive to satisfactory growth of the microorganism, for example, between about 18° and 40° C., and preferably between about 20° and 28° C. Ordinarily, optimum production of the compound is obtained in about 3 to 15 days. The medium normally remains neutral during the fermentation. The final pH is dependent, in part, on the buffers present, if any and in part on the initial pH of the culture medium.

When growth is carried out in large vessels and tanks, it is preferable to use the vegetative form, rather than the spore form, of the microorganism for inoculation to avoid a pronounced lag in the production of the new compound and the attendant inefficient utilization of the equipment. Accordingly, it is desirable to produce a vegetative inoculum in a nutrient broth culture by inoculating this broth culture with an aliquot from a soil, liquid $N_2$ agar plug, or a slant culture. When a young, active vegetative inoculum has thus been secured, it is transferred aseptically to large vessels or tanks. The medium in which the vegetative inoculum is produced can be the same as, or different from, that utilized for the production of the new compound, so long as a good growth of the microorganism is obtained.

A variety of procedures can be employed in the isolation and purification of the compound of the subject invention, for example, solvent extraction, partition chromatography, silica gel chromatography, liquid-liquid distribution in a Craig apparatus, adsorption on resins, and crystallization from solvents.

In a preferred recovery process the compound of the subject invention is recovered from the culture medium by separation of the mycelia and undissolved solids by conventional means, such as by filtration or centrifugation. The antibiotic is recovered from the filtered or centrifuged broth by extraction with a solvent for U-53,946, for example, ethyl acetate (preferred), n-butanol, methyl ethyl ketone, chloroform, and the like. The extraction is carried on after the filtered beer is adjusted to a pH of about 7 to about 10 with a base, for example, sodium hydroxide.

Essentially pure antibiotic U-53,946 can be obtained from U-53,946 preparations, obtained as disclosed above, by chromatographic procedures. In a preferred process, preparations of antibiotic U-53,946 are subjected to chromatographic procedures using silica gel and the solvent system chloroform-methanol-ammonium hydroxide (86:13:1 v/v). Active fractions as determined by assay against *S. aureus* are combined and evaporated to dryness to give a solid preparation of U-53,946 having an $R_f$ of 0.30.

Antibiotic U-53,946 is active against *S. aureus* and can be used to disinfect washed and stacked food utensils contaminated with this bacteria; they can also be used as disinfectants on various dental and medical equipment contaminated with *S. aureus*.

Further, U-53,946 can be used for treating breeding places of silkworms, to prevent or minimize infections which are well known to be caused by *Bacillus subtilis*.

Still further, U-53,946 can be used to control *Mycobacterium avium* which is a known producer of generalized tuberculosis in birds and rabbits.

It is to be understood that the microbiological process disclosed herein, though described in detail with reference to *Paecilomyces abruptus* sp. nov., NRRL 11,110, is not limited to this particular microorganism deposit. It is intended that any microorganism meeting the cultural characteristics disclosed herein, or substantial equivalence thereof, wherever deposited in the world, is a part of the subject microbiological process. Further, it is intended that this invention include strains or mutants of the said microorganism which can be produced by procedures well known in the art, for example, by subjecting the novel microorganism to x-ray or ultraviolet radiation, nitrogen mustard, phage exposure, and the like.

The following examples are illustrative of the process and products of the subject invention but are not to be construed as limiting. All percentages are by weight and all solvent mixture proportions are by volume unless otherwise noted.

EXAMPLE 1

Part A. Fermentation

An agar slant of *Paecilomyces abruptus* sp. nov., NRRL 11,110, is used to inoculate a series of 500-ml Erlenmyer flasks, each containing 100 ml of sterile seed medium consisting of the following ingredients:

| | |
|---|---|
| Glucose monohydrate | 25 gm/l |
| Pharmamedia* | 25 gm/l |
| Tap water q.s. | 1 liter |

*Pharmamedia is an industrial grade of cottonseed flour produced by Traders Oil Mill Company, Fort Worth, Texas.

The seed medium presterilization pH is 7.2. The seed inoculum is grown for two days at 28° C. on a Gump rotary shaker operating at 250 r.p.m. and having a 2½ inch stroke.

After 2 days incubation, the seed medium is used to inoculate (the inoculation rate is 5 ml of seed inoculum per 100 ml of fermentation medium) each of 500 ml non-stippled flasks each containing 100 ml of sterile fermentation medium consisting of the following ingredients:

| | |
|---|---|
| Glucose monohydrate | 10 gm/l |
| Dextrin | 10 gm/l |
| Soytone* | 5 gm/l |
| Distillers soluble** | 5 gm/l |
| Malt extract | 5 gm/l |
| Tap water q.s. | 1 liter |
| pH - 7.2 (presterilization) | |

*Soytone (Produced by Difco Laboratories, Detroit, Mich.).
**Distillers soluble (Brown-Forman Distillers Corp.,P.O. Box 1080, Louisville, KY 40201.

The fermentation flasks are incubated at a temperature of 28° C. on a Gump rotary shaker operating at 250 r.p.m. and having a 2½ inch stroke.

Part B. Recovery

Antibiotic U-53,946 in beers is detected and assayed by the use of thin layer chromatography (tlc) and antibacterial assays. Thin layer chromatograms are run on silica gel plates using chloroform-methanol-ammonium hydroxide (86:13:1 v/v) as the solvent system. Bioactivity is detected by bioautography using standard *S. aureus*-seeded agar trays.

Whole fermentation beer (ca. 1740 ml), obtained as described above, is filtered with the aid of diatomaceous earth as a filter aid. The filter cake is washed with 400 ml of water. The cake is discarded. The filtrate (1700 ml, pH 8.0) is adjusted to pH 10.0 with a 1.0 N sodium hydroxide solution. The aqueous solution is extracted with four 800-ml portions of ethyl acetate. The combined ethyl acetate extracts are evaporated under reduced pressure to a solid residue preparation of U-53,946; yield, 334 mg. A solution of this preparation in water (0.08 mcg/ml) inhibited L 1210 cell growth in vitro by 90%.

Part C. Purification

Nine hundred and thirty-nine mg of a solid preparation of U-53,946, obtained as disclosed above, is chromatographed on 100 g of silica gel using the solvent system chloroform-methanol-ammonium hydroxide (86:13:1) and collecting two hundred and fifty-five 5-ml fractions. Fractions 65–118 are combined and evaporated under reduced pressure to give 248 mg of product. This residue contains two materials as indicated by tlc on silica plates in chloroform-methanol-ammonium hydroxide (85:14:1). A second pool consisting of fractions 119–155 is evaporated under reduced pressure to give 300 mg of U-53,946 homogeneous by tlc as above, $R_f$ 0.30. The product obtained from pool 1 is rechromatographed, as discussed above. Those fractions containing pure U-53,946 as shown by tlc are combined and evaporated to dryness under reduced pressure; yield, 164 mg.

We claim:

1. A biologically pure culture of the microorganism *Paecilomyces abruptus* sp. nov., having the identifying characteristics of NRRL 11,110, said culture being capable of producing antibiotic U-53,946, said antibiotic in its essentially pure form:

(a) has the molecular formula $C_{61}H_{107}N_{11}O_{14}$;
   (b) has the following elemental analysis: C, 60.13, 59.73; H, 9.21, 8.92; N, 12.16, 11.97; O, 18.44;
   (c) has a specific rotation of $[\alpha]_D^{25} = -26°$ (c, 0.9175 EtOH);
   (d) is soluble in lower alcohols, for example, methanol, ethanol and butanol; ketones, for example, methyl ethyl ketone, halogenated solvents, ethyl acetate, or other ester-type solvents; and is relatively insoluble in aliphatic hydrocarbons;
   (e) has a characteristic infrared adsorption spectrum when dissolved in a mineral oil mull as shown in FIG. 1 of the drawings; and,
   (f) has a characteristic UV spectrum as shown in FIG. 2 of the drawings, in a recoverable quantity upon fermentation in an aqueous nutrient medium containing assimilable sources of carbon, nitrogen and inorganic substances.

* * * * *